United States Patent
Stashower

(10) Patent No.: US 7,895,057 B2
(45) Date of Patent: Feb. 22, 2011

(54) METHOD OF PROVIDING POST-PARTUM TREATMENT FOR ENHANCING COMFORT, PHYSICAL AND PSYCHOLOGICAL WELL-BEING

(76) Inventor: Mitchell E. Stashower, 5510 Willow Valley Rd., Clifton, VA (US) 20124

( * ) Notice: Subject to any disclaimer, the term of this patent is extended or adjusted under 35 U.S.C. 154(b) by 927 days.

(21) Appl. No.: 11/797,620

(22) Filed: May 4, 2007

(65) Prior Publication Data

US 2008/0271743 A1    Nov. 6, 2008

(51) Int. Cl.
*G06Q 10/2006* (2006.01)
(52) U.S. Cl. ............................................. 705/2; 705/3
(58) Field of Classification Search ................. 705/2–3; 4/515; 5/602
See application file for complete search history.

(56) References Cited

U.S. PATENT DOCUMENTS

| | | | | |
|---|---|---|---|---|
| 4,541,622 A * | 9/1985 | Tabuchi | ........................ | 5/602 |
| 5,007,118 A * | 4/1991 | Ebersole | ........................ | 4/515 |
| 5,014,371 A | 5/1991 | Heel | | |
| 5,065,315 A * | 11/1991 | Garcia | ........................ | 705/2 |
| 5,144,701 A | 9/1992 | Clark | | |
| 6,012,035 A * | 1/2000 | Freeman et al. | ................. | 705/2 |
| 6,463,597 B2 | 10/2002 | Ishimura | | |
| 6,497,577 B2 * | 12/2002 | Kanter | ........................ | 434/236 |
| 2002/0184052 A1 * | 12/2002 | Parker | ........................... | 705/2 |
| 2002/0194022 A1 | 12/2002 | Comite | | |
| 2004/0059184 A1 * | 3/2004 | Badarinwa | ................... | 600/26 |
| 2006/0053033 A1 * | 3/2006 | Wood | ............................. | 705/2 |
| 2006/0282288 A1 | 12/2006 | Rodriguez et al. | | |
| 2007/0038476 A1 | 2/2007 | Sternlicht | | |

OTHER PUBLICATIONS

Franzese et al.; "Hallmark Health to Offer Alternative Therapies for Newborns & for New and Expectant Mothers"; Oct. 18, 1999.*

* cited by examiner

*Primary Examiner*—Gerald J. O'Connor
*Assistant Examiner*—Teresa Woods
(74) *Attorney, Agent, or Firm*—Richard C. Litman

(57) ABSTRACT

The method of providing post-partum treatment for enhancing comfort, physical and psychological well-being includes the application of multiple therapeutic treatments to a patient, in order to provide pleasing, psychologically uplifting and beneficial treatment for the combat and alleviation of post-partum mood disorders, such as depression and anxiety. The patient is first transported from a first location to a treatment center. The treatment center includes a plurality of treatment stations, each being provided for providing distinct therapy to the patient. The patient is then seated in a mobile chair within the treatment center and a first therapy is performed on the patient in the mobile chair. The patient is transported, from treatment station to treatment station, within the mobile chair, thus reducing stress and strain on the patient during the treatments. Following treatment, the patient is transported back to the first location.

16 Claims, 3 Drawing Sheets

METHOD OF PROVIDING POST-PARTUM TREATMENT FOR ENHANCING COMFORT, PHYSICAL AND PSYCHOLOGICAL WELL-BEING

BACKGROUND OF THE INVENTION

1. Field of the Invention

The present invention relates to a multi-stage treatment method for increasing the comfort and self-image of new mothers, reducing the possibility of onset of post-partum mood disorders, such as depression and anxiety, for example, and for alleviating the effects thereof.

2. Description of the Related Art

The process of giving birth is exceptionally stressful to the mother, and often results in post-partum anxiety and depression. In addition to hormonal imbalance, the great physical changes which take place in a new mother (such as, for example, signs of the physical stress of delivery, stretch marks, physical indicators of exhaustion and the like) often cause self-image and self-esteem problems, which may result in the aforementioned depression and anxiety, or further the effects of already-present birth-related mood disorders. Hospitals rarely have facilities and provisions for therapies which are stress-relieving and improve the physical appearance of patients.

In addition to the stress and strain of the delivery process, numerous physical after-effects are common in new mothers. These effects include, for example, dry and inflamed skin, a flushed face, open pores, accumulation of sebum on the mother's face, hair and scalp, stretched, chafed and irritated abdominal skin, stretch marks in the patient's skin, brittle and dry finger and toe nails, increased muscle tension in the patient's neck and shoulders, and the like. Self-esteem and self-image problems, along with depression and anxiety, are often integrated with, or the result of, these physical problems.

It would be desirable to provide the new mother with grooming and relaxation facilities within, or within close proximity to, the hospital or birthing center, allowing for alleviation and prevention of post-partum mood disorders. Though hospitals provide a wide variety of medical services, including dermatological services, these are not specifically directed to the particular needs of a new mother. None of the above inventions, taken either singly or in combination, is seen to describe the instant invention as claimed. Thus, a method of providing post-partum treatment to new mothers and a treatment facility employing the same solving the aforementioned problems is desired.

SUMMARY OF THE INVENTION

The method of providing post-partum treatment for enhancing comfort, physical and psychological well-being includes the application of multiple therapeutic treatments to a patient, in order to increase the comfort level and the sense of well-being of mothers during the very stressful period after giving birth. The method provides psychologically uplifting and beneficial treatment for the combat and alleviation of post-partum depression. The treatment is preferably 30 or 40 minutes in duration, and takes place in a relaxing spa-like setting. The patient is first transported from a first location to a treatment center. The treatment center includes a plurality of treatment stations, each being provided for providing distinct therapy to the patient.

Preferably, treatment begins shortly after the new mother has given birth. Thus, in the preferred embodiment, the first location is preferably the patient's hospital room. The treatment center is preferably located within the hospital, adjacent or within close proximity to the maternity ward of the hospital.

After the patient has given birth, an appointment is scheduled with the treatment center for the patient. Given that medical complications may arise following delivery, the appointment is confirmed with the treatment center and the patient prior to transport of the patient to the treatment center. Following confirmation of the appointment, the patient is given a questionnaire to fill out. Once completed, the questionnaire is given to personnel of the treatment center, and the patient may be transported to the treatment center.

Once the patient has been transported to the treatment center, the patient is seated in a mobile chair, preferably located substantially centrally within the treatment center, and a first therapy is performed on the patient in the mobile chair. The first treatment is preferably massage of the patient's hands, neck and shoulders.

Either prior to, during or following the massage, the personnel of the treatment center preferably establish a relaxing sensory mood, in the form of selectively providing and adjusting auditory and visual stimuli.

The patient is next transported to a second therapy station while still in the mobile chair. The second therapy station is preferably a hair care station. The patient's hair is washed and during the hair washing process, a scalp massage may be delivered to the patient. While the patient's hair is being washed, a manicure may be given to the patient.

The patient is transported, from treatment station to treatment station, within the mobile chair, thus reducing stress and strain on the patient during the treatments. Following the hair washing and manicure, the patient is transported to a third station, which is preferably a hairdressing station. At this third station, the patient's hair is cut and/or styled by a hairdresser. Following the hair styling, the patient is preferably given a facial steam treatment and a hand and/or foot massage.

Following the hand and/or foot massage, or during the hand and/or foot massage, skin and nail-specific medicaments, lotions and ointments are applied to the patient's skin, fingernails and toenails. Next, the patient is preferably provided with nutritional education and information, which is individualized for the specific patient. Such nutritional information preferably emphasizes the expected changes in the patient's nails and skin following the birthing process, and provides nutritional advice to minimize and alleviate these effects.

Following treatment, the patient is transported back to the first location. When the patient is released from the hospital to return to her home, outpatient care is provided to the user in form of a package or kit containing medicaments and the like, to be used at home.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is directed towards a method of providing post-partum treatment for enhancing comfort, physical and psychological well-being in a new mother. The treatment method includes the application of multiple therapeutic treatments to a patient, within the hospital, in order to provide psychologically uplifting and beneficial treatment for the combat and alleviation of post-partum depression, anxiety and other mood disorders.

Figure 1:
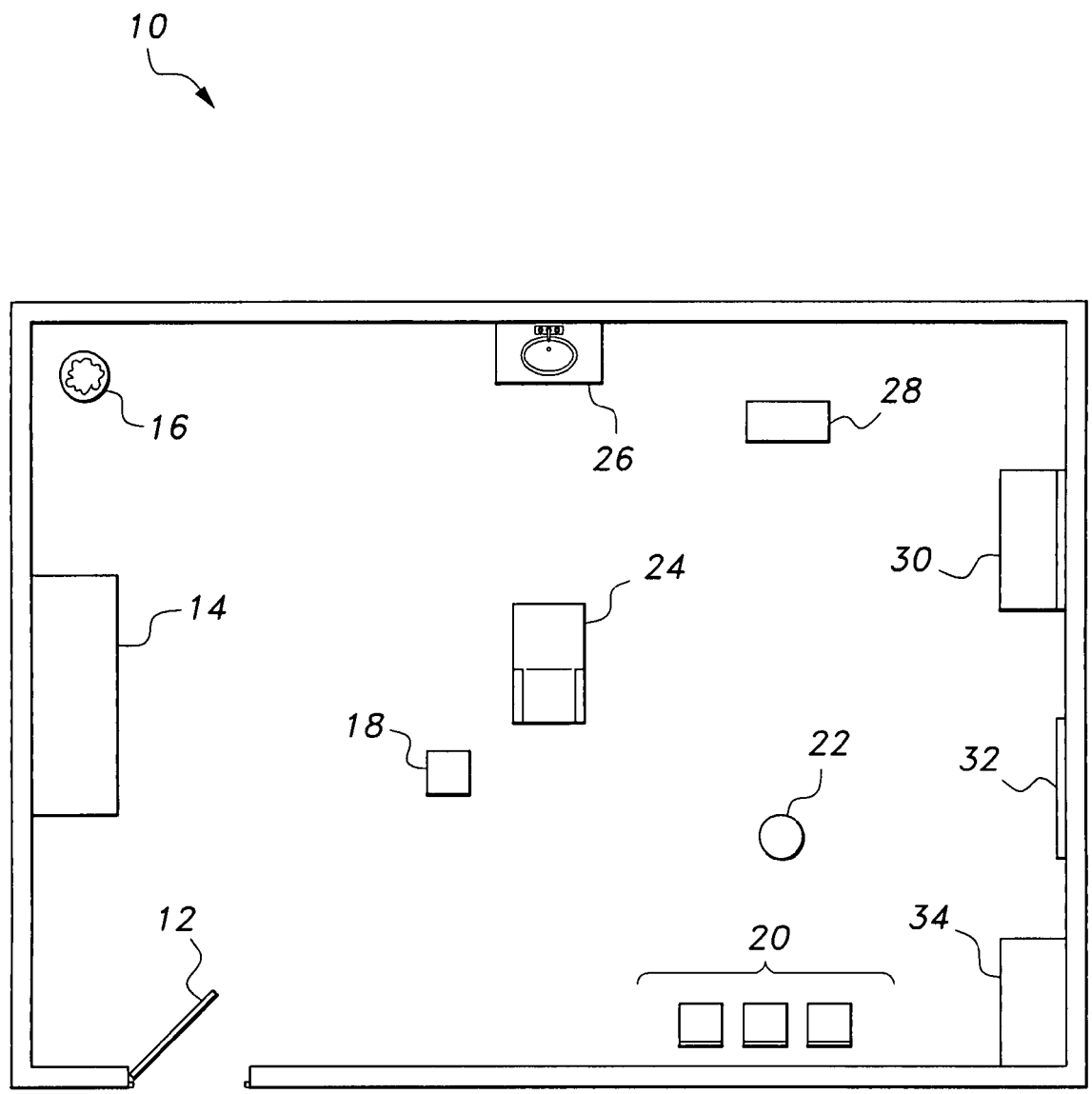
FIG. 1 is a diagrammatic view of a treatment center associated with the method of providing post-partum treatment according to the present invention.
Figure 2:
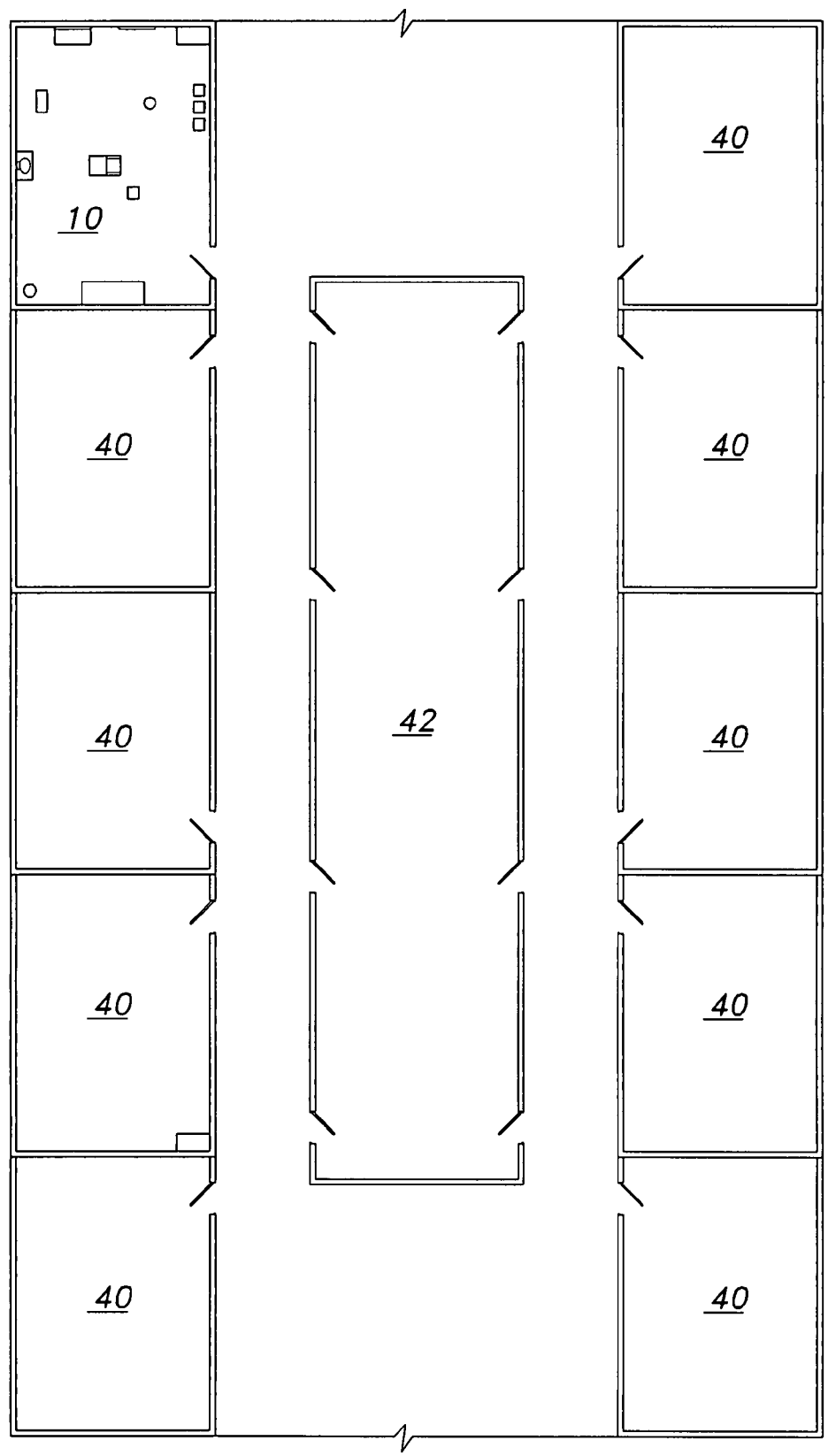
FIG. 2 is a diagrammatic view illustrating the positioning of the treatment center of FIG. 1 within a maternity ward of an exemplary hospital or birthing center.
Figure 3:
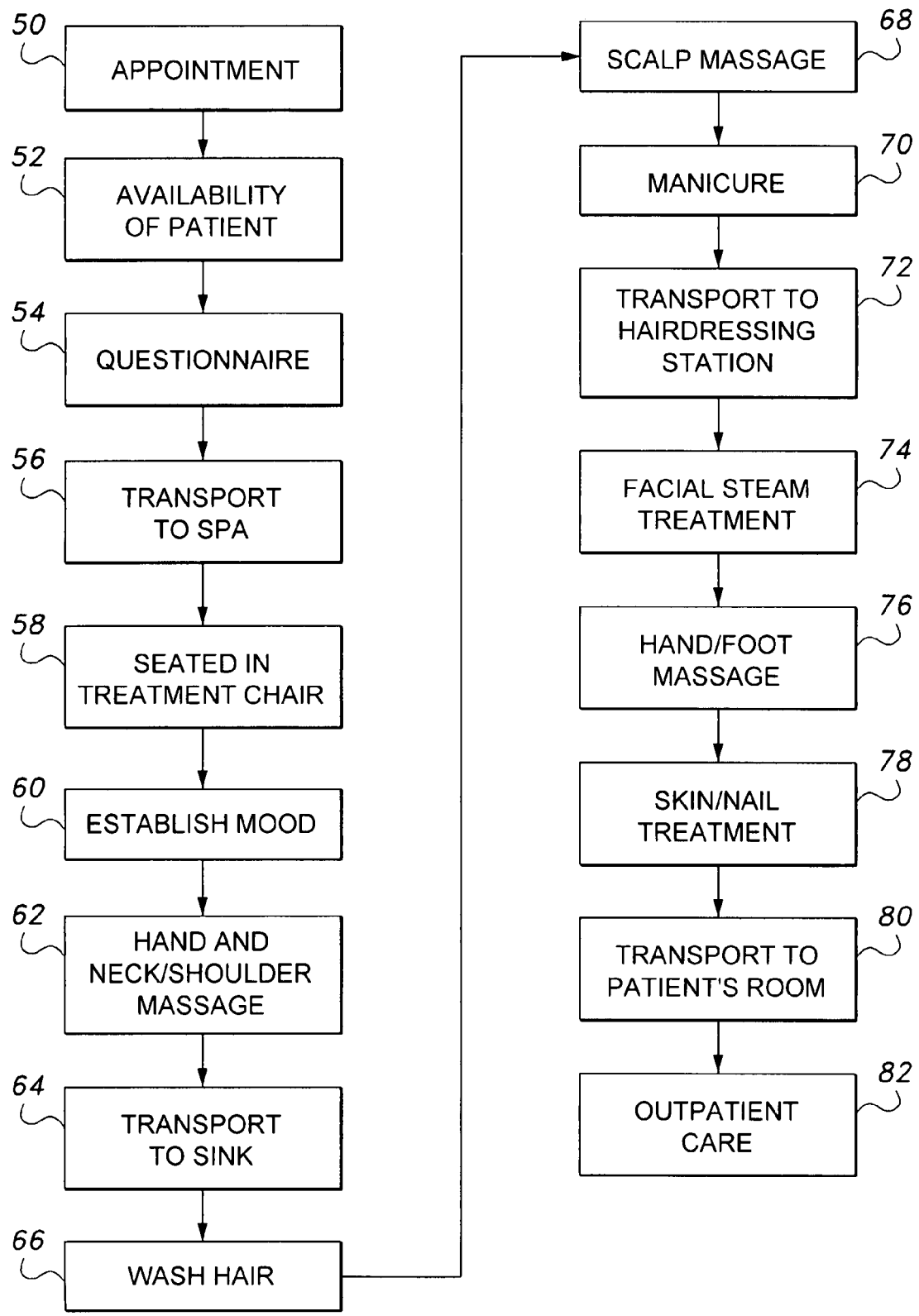
FIG. 3 is a flow diagram illustrating the method steps of the method of providing post-partum treatment according to the present invention.

As shown in FIGS. 1 and 2, the patient is initially transported from a first location to a treatment center 10. The treatment center 10 includes a plurality of treatment stations (to be described in detail below), each being provided for providing distinct therapy to the patient. Preferably, treatment begins shortly after the new mother has given birth. Thus, in the preferred embodiment, the first location is preferably the patient's hospital room. As shown in FIG. 2, the treatment center 10 is preferably located within the hospital (or other birthing center), adjacent or within close proximity to the maternity ward of the hospital. In FIG. 2, a plurality of patient rooms 40 are illustrated, with a central nursing care station 42 being provided. The treatment center 10 is shown as being positioned at one end of the residential ward. It should be understood, however, that the treatment center 10 may be located at any suitable location, and that the first location may be any suitable location, from which the patient is being transported.

After the patient has given birth, an appointment is scheduled with the treatment center for the patient. Given that medical complications may arise following delivery, the timing and medical appropriateness of the appointment is confirmed by the treatment center 10 (in conjunction with nursing station 42), and the patient prior to transport of the patient to the treatment center 10. The confirmation may take place approximately 15 minutes prior to the scheduled appointment, or any other suitable time period.

Following confirmation of the appointment, the patient is given a questionnaire to fill out. The questionnaire includes medical information, such as allergies and medical risks, for example, questions regarding the desired scope of therapeutic services, the patient's expectations and the like. Once completed, the questionnaire is given to personnel of the treatment center 10, and the patient may be transported to the treatment center 10. In FIG. 1, treatment center 10 is shown as being accessed by door 12, which leads to the hallway of the maternity ward shown in FIG. 2. Transport to treatment center 10 may include the patient walking into the treatment center, or being transported via a wheelchair or the like. The patient may bring guests with her, who may sit in provided chairs 20. Personnel of the treatment center 10 preferably include medical doctors and specially trained therapeutic specialists.

Once the patient has been transported to the treatment center 10, the patient is seated in a mobile chair 24, preferably located substantially centrally within the treatment center 10, and a first therapy is performed on the patient in the mobile chair. The first treatment is preferably massage of the patient's hands, neck and shoulders. The mobile chair 24 is preferably a mobile massage chair, providing the personnel with access to the patient's body parts to be massaged and manipulated, and further providing the patient with lumbar support, comfort and physically and psychologically beneficial support.

A massage therapist may sit on a stool or other support 22, which is positioned adjacent the initial position of chair 24. Any number of personnel and treatment specialists may be provided, dependent upon the particular needs and desires of the users. For example, two massage therapists may be provided, with a first therapist providing a hand massage, and a second therapist simultaneously providing the neck and shoulder massage.

Either prior to, during or following the massage, the personnel of the treatment center 10 preferably establish a relaxing sensory mood, in the form of selectively providing and adjusting auditory and visual stimuli. Visual stimulation may include relaxing lighting, the presence of ornamentation such as, for example, plants 16 and artwork 32 (shown in FIG. 1), or any other desired form of visual stimuli. Audio stimulation may be provided in the form of relaxing music or the like, which may be pre-recorded and played on any suitable audio player. A CD player, radio or the like may be housed within a storage cabinet 14, or positioned on a desk 34. The nature of the sensory stimulation is dependent upon the particular needs and desires of the users.

The patient is next transported to a second therapy station while still in the mobile chair 24. The second therapy station is preferably a hair care station. The second station preferably includes a hair-washing sink 26, as shown in FIG. 1. It should be understood that the particular nature of the therapeutic stations, and the therapies associated with each station, is dependent upon the particular needs and desires of the patient.

Mobile chair 24 is preferably adjustable, allowing for the chair to be reclined and positioned, such that the patient will not have to leave the chair during the entire multi-stage therapy process. The patient's hair is washed at sink 26 and during the hair washing process, a scalp massage may be delivered to the patient. While the patient's hair is being washed, a manicure may be given to the patient. Stool or support 22 is preferably also mobile, allowing for positioning adjacent the mobile chair 24 during the entire multi-treatment process. Similarly, manicure table 18 is preferably mobile, allowing the table to be positioned adjacent the patient during the hair washing process at sink 26.

The patient is transported, from treatment station to treatment station, within the mobile chair 24, thus reducing stress and strain on the patient during the treatments. Following the hair washing and manicure, the patient is transported to a third station, which is preferably a hairdressing station 30. The hairdressing station preferably includes a mirror, storage space and other conventional hairdressing elements and features, dependent upon the particular needs and desires of the users. At this third station 30, the patient's hair is cut and/or styled by a hairdresser. Following the hair styling, the patient is preferably given a facial steam treatment and a hand and/or foot massage. The facial steamer 28 is preferably mobile, allowing it to be positioned adjacent the mobile chair 24, which allows the patient to remain seated through the entire treatment process. The facial steamer 28 provides for deep pore facial treatment.

Following the hand and/or foot massage, or during the hand and/or foot massage, skin and nail-specific medicaments, lotions and ointments are applied to the patient's skin, fingernails and toenails. The ointments and medicaments may include moisturizers; hand, nail and foot rejuvenation treatments; and anti-stretch mark treatment creams, which are generally applied to the patient's abdomen.

Next, the patient is preferably provided with nutritional education and information, which is individualized for the specific patient. Such nutritional information preferably emphasizes the expected changes in the patient's skin, hair and nails following the birthing process, and provides nutritional advice to minimize and alleviate these effects.

Following treatment, the patient is transported back to the first location 40. When the patient is released from the hospital to return to her home, outpatient care is provided to the user in the form of a package or kit containing medicaments and the like, to be used at home. The above treatment results in providing the new mother with a relaxing experience, preferably providing her with a rejuvenated mood and appearance following the stress and strain of delivery.

The above process provides comprehensive cosmetic and relaxation services designed specifically to increase the psychological comfort level following the immense strain and stress of delivery. Improvement in self-image and general mood cause the patient to be far less susceptible to post-partum mood disorders, such as depression and anxiety.

Although, in the preferred embodiment, the patient is initially located in a hospital room or the like and is transported to the treatment center, it should be understood that the patient may visit the treatment center from another location; i.e., following the patient's release from the hospital, the patient may return to the hospital specifically for treatment in the treatment center. Further, it should be understood that the patient may make plural visits to the treatment center, dependent upon the particular needs and desires of the patient and the patient's caregivers.

It is to be understood that the present invention is not limited to the embodiments described above, but encompasses any and all embodiments within the scope of the following claims.

I claim:

1. A method of providing post-partum treatment for enhancing comfort, physical and psychological well-being of a patient shortly after the birth of the child and prior to discharge, comprising the steps of:
    transporting the patient from a first location to a treatment center after a medically approved period after the birth of the child and prior to discharge, the treatment center including a plurality of treatment stations located within the treatment center, each of the treatment stations providing distinct therapy to the post-partum patient, the therapies including at least massaging the patient, styling the patient's hair, and applying skin care medicaments to the patient's skin;
    selectively adjusting the sensory mood of the treatment center; the sensory mood including at least auditory and visual stimuli;
    providing a mobile chair comfortably seating the patient;
    seating the patient in the mobile chair;
    performing a first therapy on the patient in the mobile chair, wherein the first therapy includes at least the step of massaging the patient;
    transporting the patient to a second therapy station in the mobile chair;
    performing the second therapy on the patient;
    transporting the patient to a third therapy station in the mobile chair;
    performing the third therapy on the patient; and,
    transporting the patient from the therapy center to the first location, whereby the method of providing post-partum treatment for enhancing comfort, physical and psychological well-being is provided for the prevention and treatment of post-partum mood disorders selected from the group consisting of: depression, dysphoric mood, anxiety and combinations thereof.

2. The method of providing post-partum treatment for enhancing comfort, physical and psychological well-being as recited in claim 1, further comprising the step of: prior to said step of transporting the patient to the treatment center, scheduling an appointment at the treatment center for the patient.

3. The method of providing postpartum treatment for enhancing comfort, physical and psychological well-being as recited in claim 2, further comprising the step of confirming the availability of the patient prior to said step of transporting the patient.

4. The method of providing post-partum treatment for enhancing comfort, physical and psychological well-being as recited in claim 3, further comprising the steps of:
    providing a medical questionnaire to the patient;
    filling out the medical questionnaire; and,
    delivering the completed medical questionnaire to personnel of the treatment center.

5. The method of providing post-partum treatment for enhancing comfort, physical and psychological well-being as recited in claim 1, wherein the second therapy includes the step of styling the patient's hair.

6. The method of providing post-partum treatment for enhancing comfort, physical and psychological well-being as recited in claim 5, wherein the third therapy includes the step of applying skin care medicaments to the patient's skin.

7. The method of providing post-partum treatment for enhancing comfort, physical and psychological well-being as recited in claim 6, further comprising the step of applying nail treatment medicaments to the patient's finger and toe nails.

8. The method of providing post-partum treatment for enhancing comfort, physical and psychological well-being as recited in claim 6, further comprising the steps of:
    providing the patient with nutritional information; and,
    providing the patient with medicaments for use following release from the treatment center.

9. The method of providing post-partum treatment for enhancing comfort, physical and psychological well-being as recited in claim 5, wherein said step of styling the patient's hair includes washing the patient's hair.

10. The method of providing post-partum treatment for enhancing comfort, physical and psychological well-being as recited in claim 9, wherein said step of styling the patient's hair further includes massaging the patient's scalp.

11. The method of providing post-partum treatment for enhancing comfort, physical and psychological well-being as recited in claim 10, further comprising the step of providing the patient with a manicure.

12. The method of providing post-partum treatment for enhancing comfort, physical and psychological well-being as recited in claim 11, further comprising the step of applying steam to the patient's face for a facial treatment.

13. The method of providing post-partum treatment for enhancing comfort, physical and psychological well-being as recited in claim 12, further comprising the step of massaging the patient's hands.

14. The method of providing post-partum treatment for enhancing comfort, physical and psychological well-being as recited in claim 13, further comprising the step of massaging the patient's feet.

15. The method of providing post-partum treatment for enhancing comfort, physical and psychological well-being as recited in claim 1, wherein said step of massaging the patient includes massaging the patient's neck.

16. The method of providing post-partum treatment for enhancing comfort, physical and psychological well-being as recited in claim 15, wherein said step of massaging the patient further includes massaging the patient's shoulders.

* * * * *